US008604256B2

(12) United States Patent
Berretta et al.

(10) Patent No.: US 8,604,256 B2
(45) Date of Patent: Dec. 10, 2013

(54) METHOD FOR REDUCING THE FORMATION OF BY-PRODUCT DINITROBENZENE IN THE PRODUCTION OF MONONITROBENZENE

(75) Inventors: Sergio Berretta, Vancouver (CA); David A. Boyd, Vancouver (CA)

(73) Assignee: Noram International Limited, Dublin (IE)

( * ) Notice: Subject to any disclaimer, the term of this patent is extended or adjusted under 35 U.S.C. 154(b) by 278 days.

(21) Appl. No.: 13/129,023

(22) PCT Filed: Nov. 14, 2008

(86) PCT No.: PCT/CA2008/001996
§ 371 (c)(1), (2), (4) Date: May 12, 2011

(87) PCT Pub. No.: WO2010/054462
PCT Pub. Date: May 20, 2010

(65) Prior Publication Data
US 2011/0218368 A1    Sep. 8, 2011

(51) Int. Cl.
*C07C 205/00*    (2006.01)
(52) U.S. Cl.
USPC ............................................ 568/939; 568/927
(58) Field of Classification Search
None
See application file for complete search history.

(56) References Cited

U.S. PATENT DOCUMENTS

| 4,021,498 | A | 5/1977 | Alexanderson et al. |
| 5,616,818 | A | 4/1997 | Pirkl et al. |
| 7,495,136 | B2 | 2/2009 | Pohl et al. |
| 2003/0055300 | A1* | 3/2003 | Chrisochoou et al. ........ 568/937 |

FOREIGN PATENT DOCUMENTS

| EP | 0436443 | A2 | 1/1991 |
| JP | 2008-24706 | A | 2/2008 |
| WO | 2007054293 | A1 | 5/2007 |

OTHER PUBLICATIONS

Quadros, Paulo A. et al., "Continuous adiabatic industrial benzene nitration with mixed acid at a pilot plant scale", Chemical Engineering Journal 108, (2005) 1-11.
Quadros, Paulo A. et al., "Different Modeling Approaches for a Heterogeneous Liquid-Liquid Reaction Process", Ind. Eng. Chem. Res. 2005, 44, 9414-9421.
English Translation of WO 2007054293 A1, filed Nov. 7, 2006, published May 18, 2007, Applicant: Agrolinz Melamine International GmbH (15 pages).
International Search Report—completed Jul. 15, 2009, mailed Jul. 28, 2009; Application No. PCT/CA2008/001996, filed Nov. 14, 2008, Applicant: Noram International Limited.

* cited by examiner

*Primary Examiner* — Sudhakar Katakam
(74) *Attorney, Agent, or Firm* — McKee, Voorhees & Sease, P.L.C.

(57) ABSTRACT

A method for making mononitrobenzene using a plug flow reactor train. Benzene, nitric acid and sulfuric acid are introduced into the reactor and produced mononitrobenzene is removed at an outlet end. All of the benzene and at least part of the sulfuric acid are introduced at the inlet end of the reactor. A first portion of the nitric acid is introduced by a first nitric acid feed into the inlet end and a second portion of the nitric acid is introduced at one or more additional feeds that are spaced between the inlet end and the outlet end. The method results in reduced formation of by-product dinitrobenzene, improving the reaction yield of mononitrobenzene while avoiding the need for a distillation step.

10 Claims, 1 Drawing Sheet

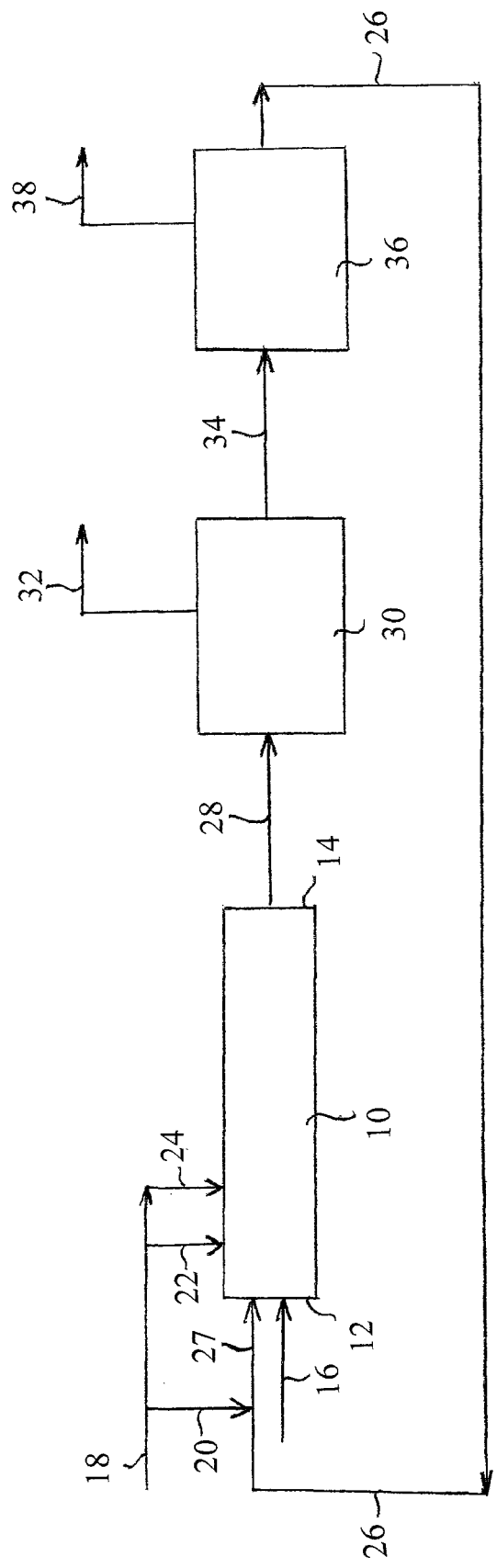

METHOD FOR REDUCING THE FORMATION OF BY-PRODUCT DINITROBENZENE IN THE PRODUCTION OF MONONITROBENZENE

CROSS-REFERENCE TO RELATED APPLICATIONS

This is a National Phase application claiming priority, to PCT/CA2008/001996 filed Nov. 14, 2008, herein incorporated by reference in their entireties.

FIELD OF THE INVENTION

The invention pertains to methods and apparatuses for manufacturing mononitrobenzene so as to minimize the formation of by-product dinitrobenzene.

BACKGROUND OF THE INVENTION

Mononitrobenzene is made industrially by mixing benzene and nitric acid in the presence of sulfuric acid as a reaction catalyst. The majority of mononitrobenzene is produced in adiabatic units using either a series of continuous stirred tank reactors (CSTR) or a plug flow reactor. In the adiabatic process, the heat of reaction is used to reconcentrate the spent sulfuric acid catalyst. Both the nitric acid and benzene reactants and the sulfuric acid are introduced at the reactor entrance.

When benzene and nitric acid are reacted to make mononitrobenzene, some well known by-products are formed, among them, nitrophenols and dinitrobenzene. These by-products are made, though at different levels, regardless of the technology used. The amount of nitrophenol formed is typically an order of magnitude higher than that of dinitrobenzene, and much research effort has been invested through the years in reducing this unwanted by-product.

Reducing the formation of dinitrobenzene has received less research attention. It is known by industrial producers of mononitrobenzene that the formation of dinitrobenzene can be slightly reduced by the introduction of a molar excess of benzene feed over nitric acid feed, and reduced somewhat more by changing the concentration of the catalytic sulfuric acid. The latter effect is described in U.S. Pat. No. 4,021,498 Alexanderson et al. For example, Alexanderson et al. indicates that higher concentrations of dinitrobenzene are produced if the sulfuric acid concentration is in excess of 72 wt %. The data of the Alexanderson et al. patent also suggest that changing the average reaction temperature affects the formation of dinitrobenzene. However a reduction of average reactor temperature is accompanied by a reduction in the kinetics of mononitrobenzene formation.

Dinitrobenzene formation consumes mononitrobenzene and nitric acid and thereby reduces the yield of product mononitrobenzene. Further, most industrial mononitrobenzene is hydrogenated to make aniline, and dinitrobenzene in mononitrobenzene is suspected of poisoning the catalyst of industrial aniline reactors.

When low dinitrobenzene concentrations are required in the product mononitrobenzene, the current industrial method used is distillation of the product mononitrobenzene. This process step is energy intensive, and requires a purge of dinitrobenzene with mononitrobenzene, which further lowers the yield of benzene to mononitrobenzene. However, it is used because there are currently no other practical methods available to produce industrial mononitrobenzene in adiabatic nitration with low dinitrobenzene concentration.

SUMMARY OF THE INVENTION

The invention provides a method for making mononitrobenzene in which only a low concentration of dinitrobenzene by-product is produced. The method thus improves the reaction yield of mononitrobenzene while also avoiding the need for a distillation step as in the prior art process, with its attendant energy input and yield loss.

According to one embodiment of the invention, there is provided an adiabatic method of making mononitrobenzene in which benzene, nitric acid and sulfuric acid are introduced into a plug flow reactor train and a product stream comprising produced mononitrobenzene is removed at the outlet end thereof. Substantially all of the benzene and some or all of the sulfuric acid are introduced at the inlet end of the reactor train. A first portion of the nitric acid is introduced into the inlet end of the reactor train by a first nitric acid feed and a second portion of the nitric acid is introduced into the reactor train at one or more feeds that are spaced between the inlet end and the outlet end. All of the sulfuric acid is introduced at the inlet end, or, alternatively, a portion of the sulfuric acid may be mixed with the second portion of the nitric acid prior to introducing the second portion of the nitric acid into the reactor, or alternatively a portion of the sulfuric acid may be fed into the reactor train downstream of the inlet end.

The invention further provides an apparatus for conducting an adiabatic reaction for making mononitrobenzene. The reactor train of the apparatus has an inlet end for receiving substantially all of the benzene and some or all of the sulfuric acid catalyst used in the reaction, and an outlet end for removing a product stream comprising produced mononitrobenzene. The apparatus includes a first nitric acid feed for introducing a first portion of the nitric acid into the inlet end, and one or more additional nitric acid feeds for introducing a second portion of the nitric acid, spaced between the inlet end and the outlet end. Alternatively, the apparatus may include means for mixing a portion of the sulfuric acid with the second portion of the nitric acid.

The reactor train comprises a plug flow reactor, or, alternatively, it comprises a reactor train in which a portion thereof has plug flow conditions present.

BRIEF DESCRIPTION OF THE DRAWING

FIG. 1 is a schematic drawing of a plug flow reactor apparatus according to the invention.

DESCRIPTION OF THE PREFERRED EMBODIMENTS

Referring to FIG. 1, the plug flow reactor 10 is an elongated tube having an inlet end 12 and an outlet end 14. A benzene conduit 16 feeds into the inlet end 12. A sulfuric acid conduit 26 for feeding reconcentrated sulfuric acid into the reactor (as further described below) also feeds into the inlet end 12. A nitric acid conduit 18 feeds nitric acid into the plug flow reactor 10 at three positions along its length, namely through the conduit 20 into the sulfuric acid conduit 26, forming mixed acid in the inlet conduit 27, which feeds into the inlet end 12 of the reactor; secondly, through the conduit 22 to feed nitric acid into the reactor at a position about one-sixth of the length from the inlet end 12 to the outlet end 14 of the reactor; and thirdly, through the conduit 24 to feed nitric acid into the reactor at a position about one-third of the length from the inlet end 12 to the outlet end 14 of the reactor. An outlet conduit 28 leads from the outlet end 14 of the reactor for transferring the product stream to a separator 30 for separating the produced mononitrobenzene from a sulfuric acid and water solution. The mononitrobenzene conduit 32 provides for the exit of produced mononitrobenzene from the separator 30. A conduit 34 provides for the transfer of the separated sulfuric acid and water to a sulfuric acid concentrator 36. A water conduit 38 provides for the removal of water from the concentrator and the conduit 26 provides for the recirculation of the concentrated sulfuric acid to the inlet end of the reactor. The recirculation loop includes a sulfuric acid makeup source (not shown).

In operation, the nitric acid feed is split into three flows into the reactor, through conduits 20, 22 and 24, in a selected flow ratio. The flows may be equal or unequal. Benzene and sulfuric acid are fed into the reactor. The flow of nitric acid (100% basis) introduced into the reactor 10 at each of the three locations is preferably between 0.01 and 8% by weight of the sulfuric acid flow rate. The reactor average temperature is in the range of 60 to 130° C. The reaction product stream is fed into the separator 30, which produces a mononitrobenzene stream through the conduit 32. The separated sulphuric acid and water is fed into the sulfuric acid concentrator, which separates out the water and produces reconcentrated sulfuric acid for use in the nitration process.

In an alternative embodiment of the apparatus, a conduit (not shown) is provided between the sulfuric acid conduit 26 and the nitric acid conduit 22. This permits a portion of the sulfuric acid to be mixed with the portion of nitric acid being fed into the reactor 10 through conduit 22.

In another alternative embodiment of the apparatus, a conduit (not shown) is provided between the sulphuric acid conduit 26 and a sulphuric acid feed located at a position between the inlet end and the outlet end of the reactor. This permits a portion of the sulphuric acid to be introduced directly into the reactor downstream of the inlet end of the reactor, while another portion is introduced at the inlet end.

Example 1

As a control experiment, an industrial adiabatic plug flow reactor producing nitrobenzene was operated at steady state under the following conditions: sulfuric acid strength at the entrance to the reactor was 70 wt %; all benzene and nitric acid feed were introduced at the reactor entrance; the reactor entrance temperature was 100° C.; the nitric acid concentration in the mixed acid at the entrance to the reactor was 1.6 wt %; benzene was introduced in molar excess. Under these conditions the produced mononitrobenzene contained 241 ppm of dinitrobenzene.

Example 2

The industrial reactor of Example 1 was modified by splitting the nitric acid feed. The split was as follows: 80% of the nitric acid was introduced at the entrance of the reactor, and the remainder of the nitric acid was introduced at a location approximately one third up the length of the reactor. The other reaction conditions were the same as in Example 1. Analysis showed that the produced mononitrobenzene contained 205 ppm of dinitrobenzene.

Example 3

The reaction of Example 2 was repeated while changing only the ratio of the nitric acid split. The nitric acid split was 60% at the entrance to the reactor with the remainder introduced one-third up the length of the reactor. Analysis showed that the produced mononitrobenzene contained 177 ppm of dinitrobenzene.

Example 4

A stirred laboratory-scale adiabatic reactor was filled with an organic phase consisting of pure benzene and an aqueous phase consisting of 70 wt % sulfuric acid and 30 wt % water. The added benzene was sufficient to be in excess of that required by the reaction. The mixture was well mixed and the temperature increased to 100° C. Sufficient nitric acid to produce a nitric acid concentration of 2.9 wt % in the aqueous phase was then quickly introduced in the reactor (within 3 to 4 seconds). The reactor temperature increased to approximately 117° C., producing an average reaction temperature of 109° C., in approximately 1 minute. Analysis of the produced organic phase showed 94 wt % mononitrobenzene, 6 wt % benzene, and 205 ppm of dinitrobenzene.

Example 5

The stirred reactor of Example 4 was filled with an organic phase consisting of pure benzene and an aqueous phase consisting of 70 wt % sulfuric acid and 30 wt % water. The added benzene was sufficient to be in excess of that required by the reaction. The mixture was well mixed and the temperature increased to 100° C. Sufficient nitric acid to produce a nitric acid concentration of 2.9 wt % in the aqueous phase was then slowly introduced into the reactor (approximately 30 seconds), simulating an infinite number of nitric acid addition splits. The reactor temperature increased to approximately 117° C., producing an average reaction temperature of 109° C. Analysis of the produced organic phase showed 94 wt % mononitrobenzene, 6 wt % benzene, and 51 ppm of dinitrobenzene.

Example 6

The stirred reactor of Example 4 was filled with an organic phase consisting of pure benzene and an aqueous phase consisting of 70 wt % sulfuric acid and 30 wt % water. The added benzene was sufficient to be in excess of that required by the reaction. The mixture was well mixed and the temperature increased to 108° C. Sufficient nitric acid to produce a nitric acid concentration of 2.9 wt % in the aqueous phase was then quickly introduced in the reactor (within 3 to 4 seconds). The reactor temperature increased to approximately 125° C., producing an average reaction temperature of 116° C., in approximately 1 minute. Analysis of the produced organic phase showed 94 wt % mononitrobenzene, 6 wt % benzene, and 306 ppm of dinitrobenzene.

Example 7

The stirred reactor of Example 4 was filled with an organic phase consisting of pure benzene and an aqueous phase consisting of 70 wt % sulfuric acid and 30 wt % water. The added benzene was sufficient to be in excess of that required by the reaction. The mixture was well mixed and the temperature increased to 108° C. Sufficient nitric acid to produce a nitric acid concentration of 2.9 wt % in the aqueous phase was then slowing introduced into the reactor (approximately 30 seconds), simulating an infinite number of nitric acid addition splits. The reactor temperature increased to approximately 125° C., producing an average reaction temperature of 116°

C. Analysis of the produced organic phase showed 94 wt % mononitrobenzene, 6 wt % benzene, and 185 ppm of dinitrobenzene.

TABLE 1

Summary of Data for Examples 4 to 7

| Example No. | Nitric acid dosing time (seconds) | Initial temperature (° C.) | Final DNB concentration (ppm by wt) |
|---|---|---|---|
| 4 | <4 | 100 | 205 |
| 5 | 30 | 100 | 51 |
| 6 | <4 | 108 | 306 |
| 7 | 30 | 108 | 185 |

The results of Examples 2 and 3 show that splitting the nitric acid feed along the length of the reactor decreases the dinitrobenzene formation relative to introducing all of the nitric acid at the reactor entrance, as in control Example 1. The results of Examples 4 to 7 show that adding nitric acid gradually to a nitration mixture produces less dinitrobenzene than adding it quickly in a single dose. The gradual addition simulates the addition of nitric acid at different points along the reaction train. The data of Examples 4 to 7 also show that lower nitration temperatures favour lower dinitrobenzene production for the same nitric acid feed split.

Examples 4 to 7 were carried out in a batch mode in an insulated, continuously stirred reactor. From chemical reactor theory, the reaction with time in a batch stirred reactor is approximately equivalent to a reaction with distance in an ideal continuously mixed plug flow reactor. Therefore the results from these batch stirred reactor experiments more closely represent the performance of an ideal plug flow nitration reactor than a CSTR reactor.

Although the invention has been described in terms of various embodiments, it is not intended that the invention be limited to these embodiments. Various modifications within the scope of the invention will be apparent to those skilled in the art. The scope of the invention is defined by the claims that follow.

What is claimed is:

1. An adiabatic method of making mononitrobenzene by nitration of benzene using nitric acid and sulfuric acid using a reactor train comprising at least in part a plug flow reactor, the reactor train having an inlet end and an outlet end, comprising the steps of:
    introducing all of the benzene into the reactor train at the inlet end;
    introducing at least a portion of the sulfuric acid into the reactor train at the inlet end;
    introducing a first portion of the nitric acid into the reactor train at the inlet end by a first nitric acid feed and a second portion of the nitric acid into the reactor train at one or more additional nitric acid feeds spaced between the inlet end and the outlet end; and
    removing a product stream comprising produced mononitrobenzene from the reactor train at the outlet end.

2. A method according to claim 1, wherein the reactor train comprises a plug flow reactor.

3. A method according to claim 1, wherein a portion of the reactor train comprises a plug flow reactor.

4. A method according to claim 1, wherein a flow rate of the nitric acid into the reactor train at each of the nitric acid feeds is in the range of 0.01 to 8 percent by weight of a flow rate of the sulfuric acid through the reactor train.

5. A method according to claim 1, wherein substantially all of the sulfuric acid is introduced at the inlet end.

6. A method according to claim 1, wherein a first portion of the sulphuric acid is introduced at the inlet end and a second portion of the sulphuric acid is introduced into the reaction train between the inlet end and the outlet end.

7. A method according to claim 1, wherein a first portion of the sulfuric acid is introduced at the inlet end and a second portion of the sulfuric acid is mixed with the second portion of the nitric acid.

8. A method according to claim 1, wherein the reactor train is at an average temperature in the range of 60 to 130 degrees C.

9. A method according to claim 1, wherein the first portion of the nitric acid is mixed with the sulfuric acid to form mixed acid before introduction into the reactor train at the inlet end.

10. A method according to claim 1, wherein the second portion of the nitric acid is mixed with a second portion of the sulfuric acid before introduction into the reactor train between the inlet and the outlet end.

* * * * *